(12) United States Patent
Allard et al.

(10) Patent No.: US 7,967,862 B2
(45) Date of Patent: Jun. 28, 2011

(54) POSTERIOR ARTICULAR DISC AND METHOD FOR IMPLANTATION

(75) Inventors: Randall Allard, Germantown, TN (US);
Alex Kunzler, Issaquah, WA (US);
Anthony Finazzo, Lake Forest Park, WA (US); Vincent Bryan, Quincy, WA (US);
Carlos Gil, Collierville, TN (US);
Robert Conta, Mercer Island, WA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1369 days.

(21) Appl. No.: 11/460,887

(22) Filed: Jul. 28, 2006

(65) Prior Publication Data
US 2007/0118223 A1 May 24, 2007

Related U.S. Application Data

(63) Continuation of application No. 11/286,902, filed on Nov. 23, 2005, now abandoned.

(51) Int. Cl.
*A61F 2/44* (2006.01)
(52) U.S. Cl. .................................................... 623/17.11
(58) Field of Classification Search ..... 623/17.11–17.16
See application file for complete search history.

(56) References Cited

U.S. PATENT DOCUMENTS

| | | | |
|---|---|---|---|
| 4,349,921 A | 9/1982 | Kuntz | |
| 5,702,450 A | 12/1997 | Bisserie | |
| 5,928,284 A | 7/1999 | Mehdizadeh | |
| 6,019,792 A * | 2/2000 | Cauthen | 623/17.14 |
| 6,110,210 A * | 8/2000 | Norton et al. | 623/17.16 |
| 6,179,874 B1 | 1/2001 | Cauthen | |
| 6,231,609 B1 | 5/2001 | Mehdizadeh | |
| 6,572,653 B1 | 6/2003 | Simonson | |
| 6,610,093 B1 | 8/2003 | Pisharodi | |
| 6,692,495 B1 | 2/2004 | Zacouto | |
| 6,749,635 B1 | 6/2004 | Bryan | |
| 7,052,515 B2 | 5/2006 | Simonson | |
| 7,083,649 B2 | 8/2006 | Zucherman et al. | |
| 7,083,650 B2 | 8/2006 | Moskowitz et al. | |
| 7,105,024 B2 * | 9/2006 | Richelsoph | 623/17.13 |

(Continued)

FOREIGN PATENT DOCUMENTS

DE 202004015198 11/2004

(Continued)

OTHER PUBLICATIONS

Notification of Transmittal of the International Search Report and the Written Opinion of the International Searching Authority, or the Declaration dated Jun. 5, 2007 (9 pages).

*Primary Examiner* — Eduardo C Robert
*Assistant Examiner* — Elana B Fisher

(57) ABSTRACT

A method for implanting an articulating intervertebral disc prosthesis into an intervertebral disc space comprises surgically accessing the intervertebral disc space through an opening on a first lateral side of the intervertebral disc space and inserting a first half of the articulating intervertebral disc prosthesis through the opening and into the intervertebral disc space. The method further comprises inserting a second half of the articulating intervertebral disc prosthesis through the opening on the first lateral side of the intervertebral disc space and positioning the first half of the articulating intervertebral disc prosthesis on a second lateral side of the intervertebral disc space. The method also comprises positioning the second half of the articulating intervertebral disc prosthesis on the first lateral side of the intervertebral disc space.

21 Claims, 4 Drawing Sheets

U.S. PATENT DOCUMENTS

| | | |
|---|---|---|
| 2004/0138749 A1 | 7/2004 | Zucherman et al. |
| 2004/0181285 A1 | 9/2004 | Simonson |
| 2005/0033435 A1 | 2/2005 | Belliard et al. |
| 2005/0043800 A1 | 2/2005 | Paul et al. |
| 2005/0143820 A1* | 6/2005 | Zucherman et al. ........ 623/17.11 |
| 2005/0154462 A1 | 7/2005 | Zucherman et al. |
| 2005/0192671 A1 | 9/2005 | Bao et al. |
| 2005/0197702 A1 | 9/2005 | Coppes et al. |
| 2005/0256578 A1 | 11/2005 | Blatt et al. |
| 2006/0004448 A1 | 1/2006 | Casey |
| 2006/0036325 A1 | 2/2006 | Paul et al. |
| 2006/0069438 A1 | 3/2006 | Zucherman et al. |
| 2006/0069440 A1 | 3/2006 | Zucherman et al. |
| 2006/0085076 A1 | 4/2006 | Krishna et al. |
| 2006/0089717 A1 | 4/2006 | Krishna et al. |
| 2006/0178745 A1 | 8/2006 | Bartish, Jr. et al. |
| 2006/0241769 A1 | 10/2006 | Gordon et al. |
| 2006/0241771 A1 | 10/2006 | Gordon et al. |

FOREIGN PATENT DOCUMENTS

| | | |
|---|---|---|
| WO | 00/04851 | 2/2000 |
| WO | 2005/011522 | 2/2005 |
| WO | 2005/070353 | 8/2005 |

\* cited by examiner

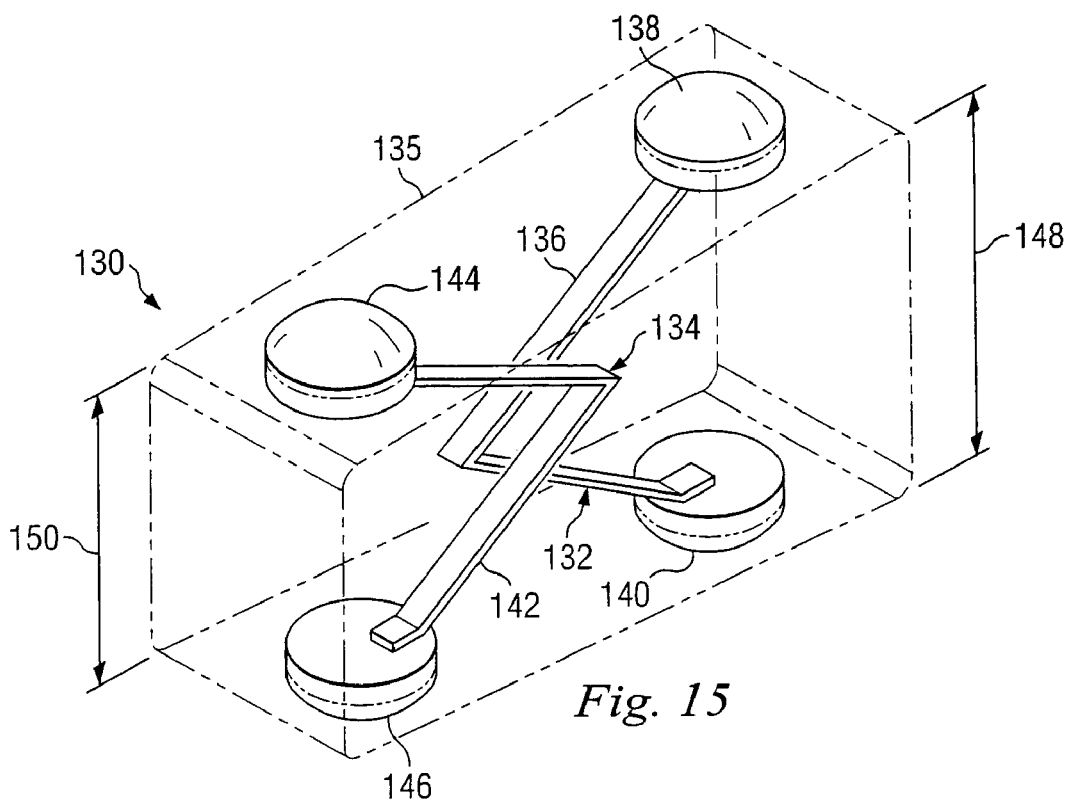
*Fig. 15*
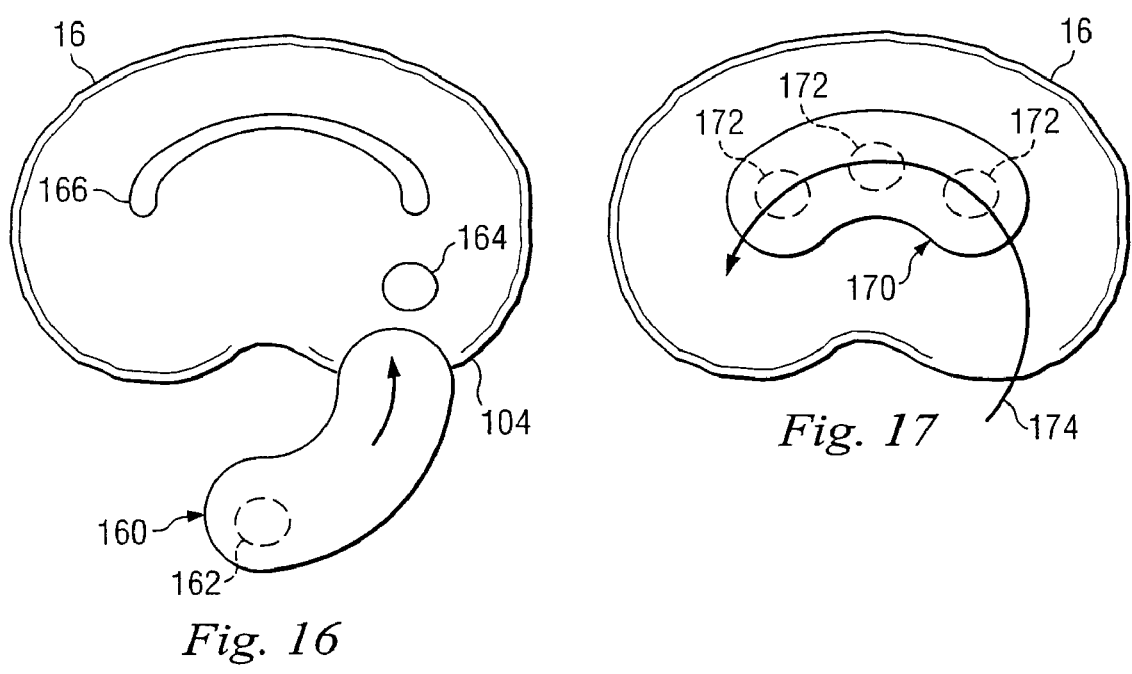
*Fig. 16*
*Fig. 17*

POSTERIOR ARTICULAR DISC AND METHOD FOR IMPLANTATION

CROSS REFERENCE

This application is a Continuation of, and claims the benefit of, U.S. patent application Ser. No. 11/286,902, entitled "Posterior Articular Disc and Method for Implantation" filed on Nov. 23, 2005, the entirety of which is incorporated by reference herein.

BACKGROUND

During the past thirty years, technical advances in the design of large joint reconstructive devices have revolutionized the treatment of degenerative joint disease, moving the standard of care from arthrodesis to arthroplasty. Progress in the treatment of vertebral disc disease, however, has come at a slower pace. Currently, the standard treatment for disc disease remains discectomy followed by vertebral fusion. While this approach may alleviate a patient's present symptoms, accelerated degeneration of adjacent discs is a frequent consequence of the increased motion and forces induced by fusion. Thus, reconstructing the degenerated intervertebral disc with a functional disc prosthesis to provide motion and to reduce deterioration of the adjacent discs may be a more desirable treatment option for many patients. To date, many spinal arthroplasty devices have, given their size and configuration, relied upon highly invasive surgical implantation through an anterior approach. Devices and methods for a less invasive posterior surgical approach may be a desirable alternative for many patients.

SUMMARY

In one embodiment, a method for implanting an articulating intervertebral disc prosthesis into an intervertebral disc space comprises surgically accessing the intervertebral disc space through an opening on a first lateral side of the intervertebral disc space and inserting a first half of the articulating intervertebral disc prosthesis through the opening and into the intervertebral disc space. The method further comprises inserting a second half of the articulating intervertebral disc prosthesis through the opening on the first lateral side of the intervertebral disc space and positioning the first half of the articulating intervertebral disc prosthesis on a second lateral side of the intervertebral disc space. The method also comprises positioning the second half of the articulating intervertebral disc prosthesis on the first lateral side of the intervertebral disc space.

In a second embodiment, an articulating intervertebral system for interposition between two vertebral endplates comprises a first half, comprising upper and lower components and a central body adapted to articulate between the upper and lower components, and a second half, comprising upper and lower components and a central body adapted to articulate between the upper and lower components. The first and second halves are adapted for implantation entirely within an intervertebral disc space between the two vertebral endplates.

In a third embodiment, a method of implanting a vertebral disc prosthesis comprises inserting a first kidney-shaped component of the vertebral disc prosthesis through a lateral opening in an annulus wall into a first position and inserting a second kidney-shaped component of the vertebral disc prosthesis through the lateral opening in the annulus wall to contact the first component and move the first component from the first position.

In a fourth embodiment, an intervertebral implant for implantation between a pair of adjacent vertebral endplates comprises a first spring member comprising a first pair of bone contacting elements. The implant further comprises a polymeric body encasing at least a portion of the first spring member, wherein the bone contacting elements are adapted to directly engage the adjacent vertebral endplates.

BRIEF DESCRIPTION OF THE DRAWINGS

FIG. 15 is a perspective view of an intervertebral implant according to another embodiment of this disclosure.

FIG. 16 is a top sectional view of an intervertebral disc space during an alternative process for implantation of an intervertebral implant.

FIG. 17 is a top sectional view of an intervertebral implant according to another embodiment of this disclosure.

DETAILED DESCRIPTION

Figure 1:
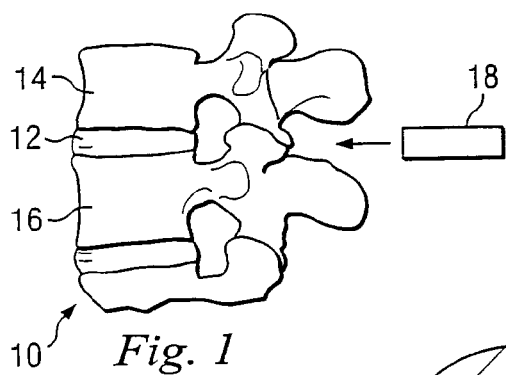
FIG. 1 is a side view of vertebral column with an intervertebral implant.

The present invention relates generally to vertebral reconstructive devices, and more particularly, to an articular disc and related methods for posterior implantation. For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Referring first to FIG. 1, the numeral 10 refers to a vertebral joint which includes an intervertebral disc 12 extending between vertebrae 14, 16. The disc 12 may be partially or entirely removed and an intervertebral implant 18 may be inserted between the vertebrae 14, 16 to preserve motion within the joint 10. Although the illustration of FIG. 1 generally depicts the vertebral joint 10 as a lumbar vertebral joint, it is understood that the devices, systems, and methods of this disclosure may also be applied to all regions of the vertebral column, including the cervical and thoracic regions. Additionally, although the illustration of FIG. 1 generally depicts a posterior approach for insertion of the implant 18, other approaches including anterior, posterolateral, lateral, and anterolateral are also contemplated. Furthermore, the devices, systems, and methods of this disclosure may be used in non-spinal orthopedic applications.

Figure 2:
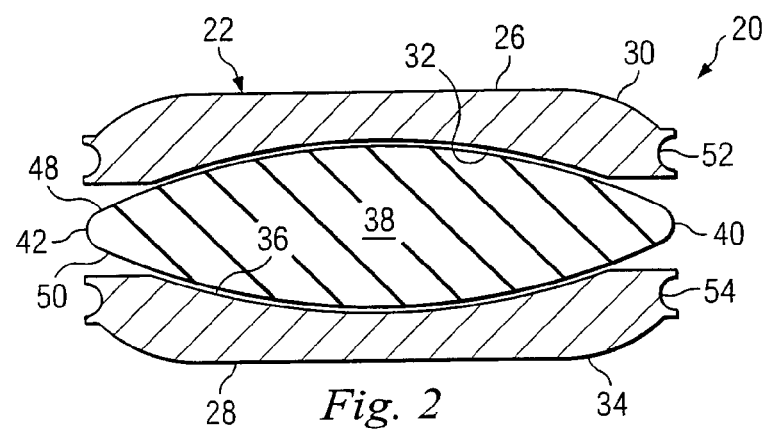
FIG. 2 is a side sectional view of an intervertebral implant according to one embodiment of this disclosure.
Figure 3:
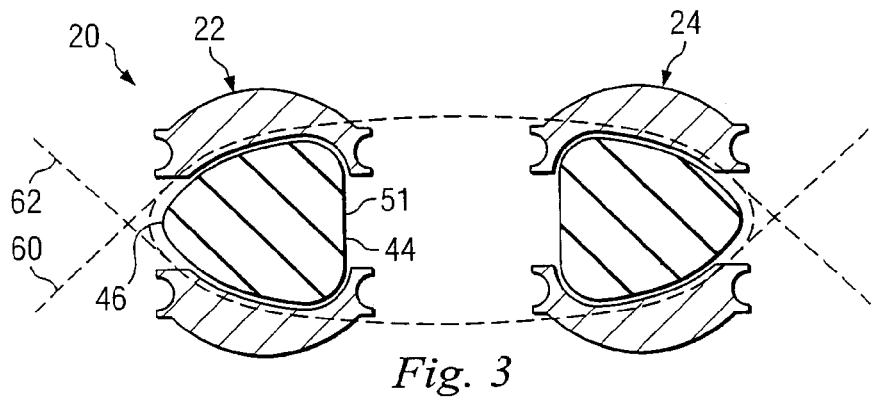
FIG. 3 is a front sectional view of the intervertebral implant depicted in FIG. 2.

Referring now to FIGS. 2 and 3, an intervertebral implant 20 may be used as the prosthesis 18 of FIG. 1 according to one embodiment of the present disclosure. The intervertebral disc prosthesis 20 includes a first articulating half 22 and a second articulating half 24. The first articulating half 22 includes endplate components 26, 28. The endplate component 26 includes an exterior surface 30 and an interior surface 32. The endplate component 28 includes an exterior surface 34 and an interior surface 36. A central component 38 may extend between the interior surfaces 32, 36. In this embodiment, the central component 38 may have a proximal end portion 40 and a distal end portion 42 as well as a right side portion 44 and a left side portion 46. The central component 38 may comprise an upper surface 48 and a lower surface 50. The upper and lower surfaces 48, 50 may curve between the proximal and distal end portions 42, 44 and may also curve between the right side portion 44 and the left side portion 46. As shown in FIG. 3, the right and left side portions 44, 46 may be asymmetric with a surface 51 extending along the right side portion 44.

The endplate components 26, 28 may further comprise grooves 52, 54, respectively, for receiving a retaining ring (not shown) for retaining a flexible sheath (not shown) between the endplate components 26, 28. These features and others which may be incorporated into the articulating half are described in greater detail in U.S. patent application Ser. No. 10/303,569 entitled, "Implantable Joint Prosthesis and Associated Instrumentation" which is incorporated by reference herein.

The endplate components 26, 28 and the central component 38 may be formed of any suitable biocompatible material including metals such as cobalt-chromium alloys, titanium alloys, nickel titanium alloys, and/or stainless steel alloys. Ceramic materials such as aluminum oxide or alumnia, zirconium oxide or zirconia, compact of particulate diamond, and/or pyrolytic carbon may be suitable. Certain polymer materials may also be used, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE. The central component 38 and the endplate components 26, 28 may be formed of different materials, thus permitting metal on metal, metal on ceramic, metal on polymer, ceramic on ceramic, ceramic on polymer, or polymer on polymer constructions. To create a smooth articulation between all contacting surfaces, all or portions of the surfaces 32, 36, 48, 50 may be ground and/or polished.

The exterior surfaces 30, 34 may include features or coatings (not shown) which enhance the fixation of the implanted prosthesis. For example, the surfaces may be roughened such as by chemical etching, bead-blasting, sanding, grinding, serrating, and/or diamond-cutting. All or portions of the exterior surfaces 26, 32 may receive a coating of a metallic substance which may be applied by sintering or by a spray coating such as a plasma spray. All or a portion of the exterior surfaces 26, 32 may also be coated with a biocompatible and osteoconductive material such as hydroxyapatite (HA), tricalcium phosphate (TCP), and/or calcium carbonate to promote bone in growth and fixation. Alternatively, osteoinductive coatings, such as proteins from transforming growth factor (TGF) beta superfamily, or bone-morphogenic proteins, such as BMP2 or BMP7, may be used. Other suitable features may include spikes for initial fixation; ridges or keels to prevent migration in the lateral and anterior-posterior direction, for example; serrations or diamond cut surfaces; fins; posts; and/or other surface textures.

The central body may, in an alternative embodiment, be both deformable and resilient, and composed of a material that has surface regions that are harder than the interior region. This would allow the central body to be sufficiently deformable and resilient that the implant functions effectively to provide resistance to compression and to provide dampening, while still providing adequate surface durability and wear resistance. In addition, the material of the central body may have surfaces that are very lubricious, in order to decrease friction between the central body and the rigid opposing shells.

In this alternative, the material used to make the central component may be a slightly elastomeric biocompatible polymeric material, which may be coated or impregnated to increase surface hardness, or lubricity, or both, as described above. Coating may be done by any suitable technique, such as dip coating, and the coating solution may include one or more polymers, including those described below for the central body. The coating polymer may be the same as or different from the polymer used to form the central body, and may have a different durometer from that used in the central body. Typical coating thickness may be greater than about 1 mil, more particularly from about 2 mil to about 5 mil. Examples of suitable materials include polyurethanes, such as polycarbonates and polyethers, such as Chronothane P 75A or P 55D (P-eth-PU aromatic, CT Biomaterials); Chronoflex C 55D, C 65D, C 80A, or C 93A (PC-PU aromatic, CT Biomaterials); Elast-Eon II 80A (Si-PU aromatic, Elastomedic); Bionate 55D/S or 80A-80A/S (PC-PU aromatic with S-SME, PTG); CarboSil-10 90A (PC-Si-PU aromatic, PTG); Tecothane TT-1055D or TT-1065D (P-eth-PU aromatic, Thermedics); Tecoflex EG-93A (P-eth-PU aliphatic, Thermedics); and Carbothane PC 3585A or PC 3555D (PC-PU aliphatic, Thermedics).

The second articulating half 24 may be substantially similar to the half 22 and therefore will not be described in detail. The implant 20 may be implanted into the intervertebral space between vertebral bodies 14 and 16 using one of the techniques that will be described in detail below.

After implantation, the articulating halves 22, 24 may be arranged generally parallel to one another with, for example, the distal end portion 42 extending toward an anterior side of the intervertebral disc space and the proximal end portion 40 extending toward a posterior side of the intervertebral disc space. A spacing between the halves 22, 24 may prevent contact between the halves. As shown in FIG. 3, an arc of motion 60 may extend between the surfaces 32, 48 of the articulating half 22, across the spacing, and between the corresponding surfaces of the half 24. The asymmetric shape of the central component may permit this single arc of fluid motion. Similarly, an arc 62 may extend between the surfaces 36, 50 of the articulating half 22, across the spacing, and between the corresponding surfaces of the half 24. These single arcs of motion between the halves 22, 24 may allow the central components to move in concert, particularly during lateral bending motions, despite being connected by the spacing. In this embodiment, the central component 38 may articulate between the endplate components 26, 28 to permit flexion-extension motion, lateral bending motion, and at least a limited amount of torsional motion.

Figure 4:
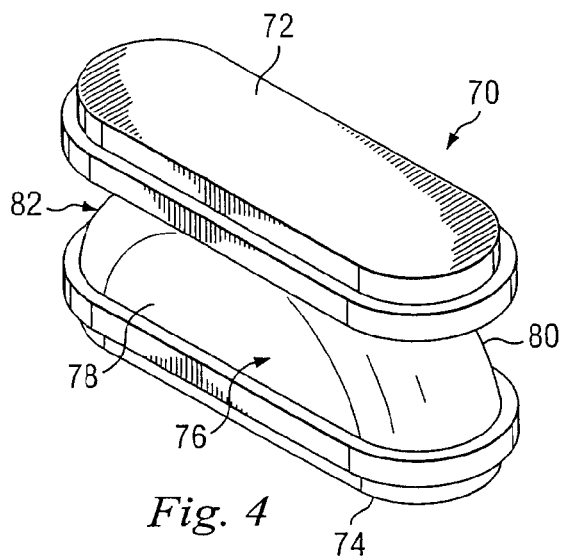
FIG. 4 is a perspective view of an intervertebral implant according to another embodiment of this disclosure.
Figure 5:
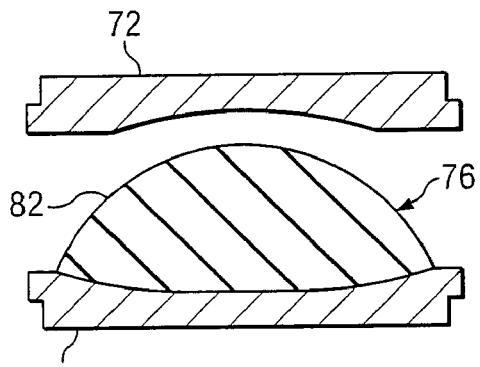
FIG. 5 is a side sectional view of the intervertebral implant depicted in FIG. 4.

Referring now to FIGS. 4 and 5, in an alternative embodiment, an articulating half 70 includes endplate components 72, 74. A central component 76 may extend between the endplate components 72, 74. In this embodiment, the central component 76 may have side surfaces 78, 80 and a curved surface 82 extending from a proximal to a distal end of the component 76 and between the side surfaces 78, 80. The endplate components 72, 74 may be formed from materials including those listed above for endplate components 26, 28. Similarly, the central component may be formed of any of the materials described above for the central component 38. The articulating half 70 may be implanted into the intervertebral disc space between vertebral bodies 14, 16 according to one of the techniques that will be described in detail below.

After implantation, the articulating half 70 may be arranged generally parallel to another similarly configured articulating half. A spacing between the halves may prevent contact. In this embodiment, the central component 76 may articulate between the endplate components 72, 74 to permit flexion-extension motion while limiting lateral bending and torsional motions.

Figure 6:
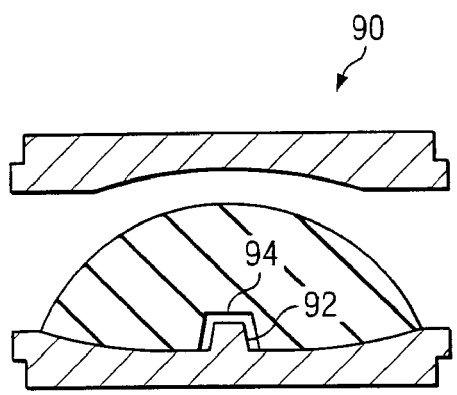
FIG. 6 is a side sectional view of an intervertebral implant according to another embodiment of this disclosure.

Referring now to FIG. 6, in this embodiment an articulating half 90 may be substantially similar to the articulating half 70 except for the differences to be described. A post 92 may extend from a lower endplate component to engage a recess 94 in an articulating central component. The post 90 may serve to limit flexion-extension motion and prevent expulsion of the central component from between the lower endplate component and an upper endplate component.

Referring now to FIGS. 7-10, a method for implanting a motion preserving intervertebral implant 100 between vertebrae 14, 16 may include the step of selecting a first half 102 of the intervertebral implant 100. In this embodiment, the first half 102 may be kidney-shaped although other shapes such as oval, oblong, and rectangular are also contemplated. The first half 102 may be a three-component articulating joint such as halves 22 or 70 described above, a two-component ball and socket style articulating joint, or a unibody component that provides motion through the use of elastomeric materials. Another step in the method for installing the implant 100 is creating an incision in the patient's back and forming a posterior unilateral opening on one lateral side 104 of the intervertebral disc space. The opening may be of any size required to accept a single implant half, for example, an 11 mm opening may be suitable. Through this opening, instrumentation may be inserted to evacuate remaining disc tissue. Instrumentation may also be inserted to mill or to otherwise dislocate bone to fashion a path, track, or recess in one or both of the endplates adjacent the intervertebral disc space. It is understood that in some embodiments, no bone removal may be needed. The disc space may be distracted during the milling procedure and/or subsequent insertion procedures.

Figure 7:
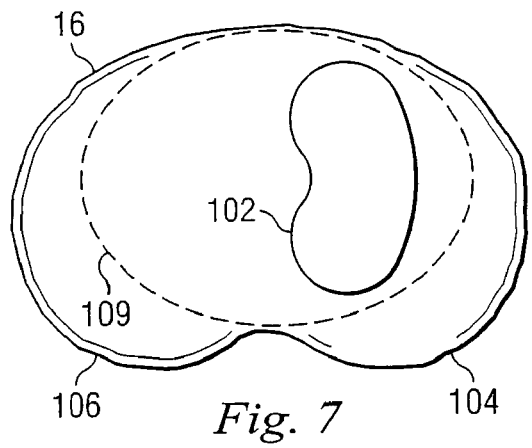
FIG. 7 is a top sectional view of an intervertebral disc space during a process for implantation of an intervertebral implant.
Figure 8:
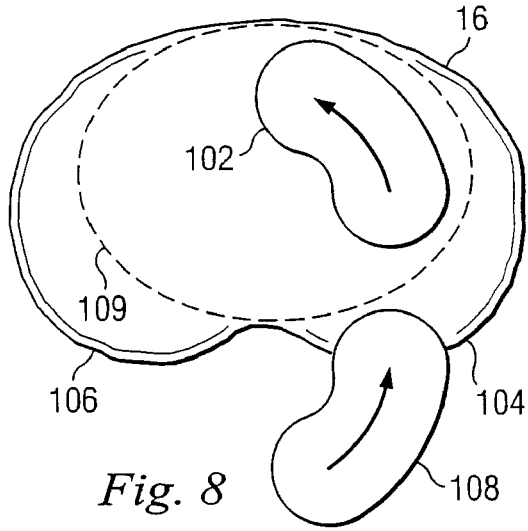
FIG. 8 is a top sectional view of an intervertebral disc space at another step in the process for implantation of an intervertebral implant.

As shown in FIG. 7, the first half 102 may be inserted through the unilateral opening on lateral side 104 of the intervertebral disc space. As shown in FIG. 8, a second half 108 of the intervertebral implant 100 may be inserted through the same unilateral opening in the lateral side 104 of the intervertebral disc space. As the second half 108 is inserted it may engage and advance the first half 102, pushing it from its original position. The first half 102 may travel along an arcuate guide path 109 or recess edge created in the endplate of vertebral body 16. In an alternative embodiment, where the bone of the endplate has not been prepared to guide the first half, the first half may be guided by the remaining annulus tissue.

Figure 9:
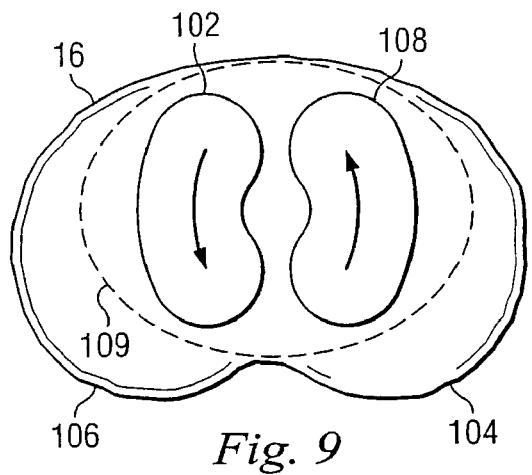
FIG. 9 is a top sectional view of an intervertebral disc space at another step in the process for implantation of an intervertebral implant.
Figure 10:
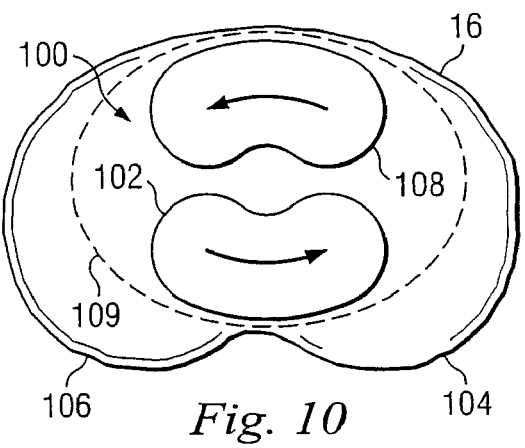
FIG. 10 is a top sectional view of an intervertebral disc space at another step in the process for implantation of an intervertebral implant.

As shown in FIG. 9, the second half 108 may be fully inserted into the first lateral side 104 of the intervertebral disc space. As the second half 108 becomes inserted, the first half 102 may continue along an arcuate path until coming to rest on the opposite lateral side 106 from side 104. As shown in FIG. 10, to mitigate the risk of the second half 108 becoming expulsed through the opening in the lateral side 104, both the first and second halves 102, 108 may continue to move along arcuate paths until first and second halves 102, 108 extend across the intervertebral disc space and into both lateral sides 104, 106. It is understood that the implant 100 may remain in the position shown in FIG. 9 with other structures or techniques (as will be described below) used to prevent expulsion of the components.

Figure 11:
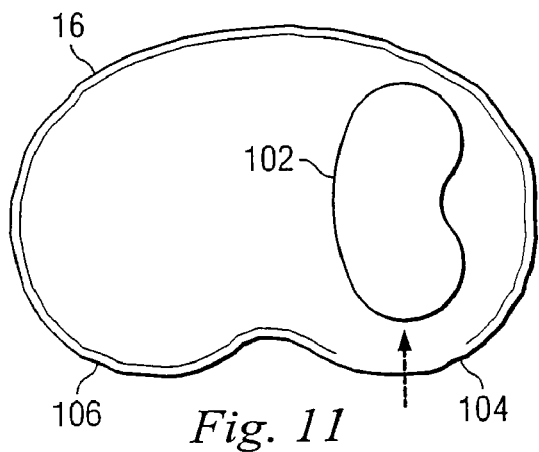
FIG. 11 is a top sectional view of an intervertebral disc space during an alternative process for implantation of an intervertebral implant.
Figure 12:
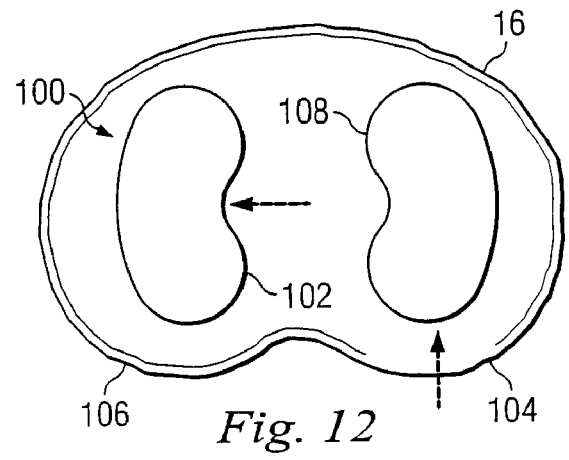
FIG. 12 is a top sectional view of an intervertebral disc space at another step in the alternative process for implantation of an intervertebral implant.

Referring now to FIGS. 11-12, the intervertebral implant 100 comprising first and second halves 102, 108 may be installed according to an alternative embodiment. As described above, a posterior unilateral opening may be created on one lateral side 104 of the intervertebral disc space. Through this opening, instrumentation may be inserted to evacuate remaining disc tissue. Instrumentation may also be inserted to mill or to otherwise dislocate bone to fashion a path or recess in one or both of the endplates adjacent the intervertebral disc space. It is understood that in some embodiments, no bone removal may be needed.

As shown in FIG. 11, the first half 102 may be inserted through the opening in the lateral side 104 and into the intervertebral disc space. As shown in FIG. 12, the first half 102 may be displaced from the lateral side 104 and shuttled to the opposite lateral side 106, and the second half 108 may be inserted through the opening in the lateral side 104 and into the intervertebral disc space. The shuttling of the first half 102 to the opposite lateral side 106 may be accomplished using an instrument or using the second half 108 as a pushing tool.

In an alternative embodiment, bilateral posterior openings, one on each lateral side 104, 106, may be created to directly insert the halves 102, 108 into their respective lateral sides 106, 104. It is understood, however, that a second opening on the opposite lateral side may require an additional incision to the patient. In still another alternative embodiment, recesses may be milled into the endplate of the vertebral body to correspond to protrusions on the implant 100. As the halves of the implant are moved within the intervertebral disc space, the protrusions may become engaged with the recesses to hold the halves in place and resist expulsion.

The use of a posterior approach such as those described above may offer the surgeon a technique similar to fusion with which he or she may already be familiar. The posterior approach may allow herniations impinging on a nerve root to be more easily decompressed. Further, later revision surgeries may be more easily managed as compared to anteriorly placed devices.

Figure 13:
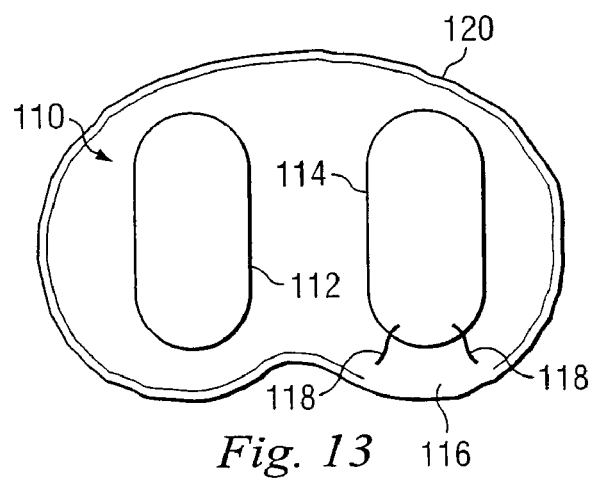
FIG. 13 is a top sectional view of an intervertebral disc space having anchored bilateral intervertebral implants.
Figure 14:
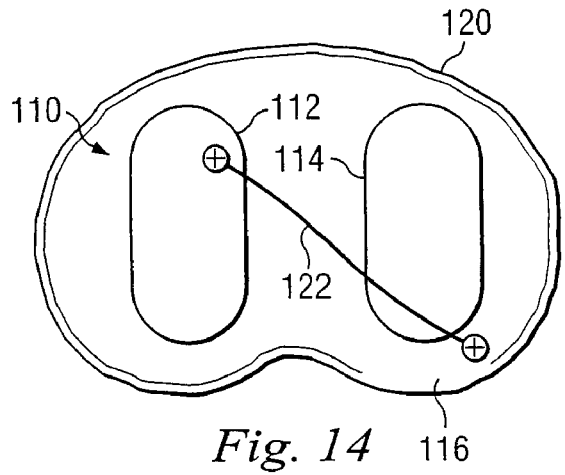
FIG. 14 is a top sectional view of an intervertebral disc space having anchored bilateral intervertebral implants.

Referring now to FIG. 13, to prevent expulsion of one or more components 112, 114 of an implant 110 through a lateral opening 116, sutures, barbs, anchors or other retaining devices 118 may be used to tether the half 114, nearest the opening 116, to either the endplate of vertebra 16 or an annulus 120. Referring now to FIG. 14, a cabling system 122 may be installed to tether the half 112 to the half 114. The cabling system 122 may be anchored to bone, annulus tissue, or simply between the two halves 112, 114. In an alternative embodiment, the opening 116 may be blocked with a suture, anchoring block or other mechanism to prevent expulsion of components of the implant 110. In still another alternative, a stepped cavity may be created. The implant half may rest within the stepped cavity such that the step limits expulsion of the implant half.

Referring now to FIG. 15, an implant half 130 comprises a first spring member 132, a second spring member 134, and a body member 135. The first spring member 132 comprises a spring arm 136 extending between two pads components 138, 140. The second spring member 134 comprises a spring arm 142 extending between two pad components 144, 146. The first and second spring members 132, 134 may be encased in the body member 135 which may, for example, be formed of molded polyurethane. Portions of the pad components 138, 140, 144, 146 may protrude from the body member 135 to engage the adjacent bony endplates of vertebrae 14, 16. The exposed portions of the pad components 138, 140, 144, 146 may be formed of titanium to promote bone ingrowth. Other materials or surface treatments (such as those described above) may also be suitable to promote bone ingrowth.

The spring members 132, 134 may be molded into the body member 135 while in at least slight compression. Thus, when implanted, the spring members 132, 134 may have a tendency to push outward, causing the pad components 138, 140, 144, 146 to engage the adjacent bone and promote bony ingrowth with the pad components 138, 140, 144, 146. The body member 135 may provide stability and separation to the spring members 132, 134.

The implant half 130 may have a lordotic angle to promote proper alignment and disc height in the remodeled disc space. For example the half 130 may have a distal height 148 which is greater than a proximal height 150. The distal height may be, for example, 14 mm and the proximal height may be, for example, 10 mm. At these exemplary heights, the lordotic angle may be approximately 8-12°. It is understood that these heights are merely examples and that in alternative embodiments the lordotic angles and the distal and proximal heights may be varied to fit a particular patient.

The implant half 130 may be installed either alone or in combination with another similarly configured implant half into the intervertebral disc space using any of the methods described above. Prior to implantation, the upper and lower endplates of the adjacent vertebrae may be prepared by creating recesses in the bone to match the location of the pad components 138, 140, 144, 146. When the implant half 130 is installed, the pad components may mate with the prepared recesses to hold the implant half 130 in place. As installed the spring members 132, 134 may exert an outward force on the adjacent endplates which promotes proper spinal alignment and encourages bone ingrowth with the pads components to provide further stability for the implant half 130.

Referring now to FIG. 16, a motion preserving intervertebral implant 160 may be substantially similar to the component halves 102, 108 of implant 100 or any of the implants described above except for the differences to be described. A convex protrusion 162 may extend from a trailing end of the inferior exterior surface of implant 160. The endplate of vertebra 16 may be milled or otherwise prepared to include a pocket 164 and a curved track 166. The implant 160 may be installed according to any of the embodiments described above with the few differences to be described. The implant 160 may be inserted through a posterior unilateral opening on lateral side 104 of the intervertebral disc space. The leading edge of the implant 160 may be guided by the track 166 until the protrusion 162 becomes located in the pocket 164. The placement of the protrusion 162 in the pocket 164 may limit displacement of the implant 160 after it reaches its final placement. In an alternative embodiment, the implant or implant half may include a pair of protrusions, one extending from each of the superior and inferior exterior surfaces. These protrusions may mate, respectively, with pockets located in the endplates of vertebrae 14 and 16. In still another alternative embodiment, the implant or implant half may include protrusions or other features that may be guided by the track 166. In still another embodiment, the leading end of the implant or implant half may be configured with a protrusion that both follows the track and becomes located in a pocket on the opposite lateral side 106 from the opening. Although the protrusions are described as convex, it is understood that other configurations such as pointed may be suitable alternatives.

Referring now to FIG. 17, a motion preserving intervertebral implant 170 may be substantially similar to the component halves 102, 108 of implant 100 or any of the implants described above except for the differences to be described. In this embodiment, the implant 170 includes a plurality of convex protrusions 172 distributed across the inferior exterior surface of implant 170 generally along a path of implantation 174. The implant 170 may be installed according to any of the embodiments described above with the specific differences to be described. The implant 170 may be inserted through a posterior unilateral opening on lateral side 104 of the intervertebral disc space. The implant 170 may follow the path of implantation 174 until the implant 170 is centered within the disc space or positioned on a desired lateral half 104 or 106. The protrusion 172 may become lodged within the unprepared surface of the bony endplate or within milled or otherwise prepared pockets previously formed in the endplate. In one alternative embodiment, the path of implantation may be milled and the protrusions permitted to follow the milled path. In still another alternative embodiment, a set of protrusions may extend from the superior exterior surface of the implant and lodge within the endplate of vertebra 14.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," "right," "anterior," "posterior," "superior," "inferior," "upper," and "lower" are for illustrative purposes only and can be varied within the scope of the disclosure. In the claims, means-plus-function clauses are intended to cover the elements described herein as performing the recited function and not only structural equivalents, but also equivalent elements.

What is claimed is:

1. A method for implanting an articulating intervertebral disc prosthesis into an intervertebral disc space, wherein the intervertebral disc space is composed of a first lateral side and a second lateral side, the method comprising:

surgically accessing the intervertebral disc space through an opening on a posterior side of the intervertebral disc space and on the first lateral side of the intervertebral disc space;

inserting a first half of the articulating intervertebral disc prosthesis through the opening and into the intervertebral disc space;

inserting a second half of the articulating intervertebral disc prosthesis through the opening, wherein the first half of the intervertebral disc prosthesis is separate from and not connected to the second half of the intervertebral disc prosthesis;

positioning the first half of the articulating intervertebral disc prosthesis on the second lateral side of the intervertebral disc space such that the entirety of the first half of the articulating disc prosthesis is situated on the second lateral side of the intervertebral disc space; and positioning the second half of the articulating intervertebral disc prosthesis on the first lateral side of the intervertebral disc space such that the entirety of the second half of the articulating disc prosthesis is situated on the first lateral side of the intervertebral disc space.

2. The method of claim 1 wherein the step of inserting the second half comprises:

engaging the first half and advancing the first half from the first lateral side of the intervertebral disc space and into the second lateral side.

3. The method of claim 1 wherein the first half takes an arcuate path from the first lateral side to the second lateral side.

4. The method of claim 3 wherein at least a portion of the arcuate path is milled into an endplate of a vertebra adjacent the intervertebral disc space.

5. The method of claim 1 wherein the first half takes a generally linear path from the first lateral side to the second lateral side.

6. The method of claim 1 wherein the intervertebral disc space is defined by two adjacent vertebral bodies, at least one of which having an anterior side that is arcuate in shape, and wherein the first half takes an arcuate path from the first lateral side to the second lateral side, wherein the arcuate path is defined by the arcuate shape of the anterior side of the at least one vertebral body.

7. The method of claim 1 further comprising displacing bone to create a passage in a vertebral endplate adjacent the intervertebral disc space.

8. The method of claim 1 further comprising locating a protrusion of the first half into a prepared depression in an endplate of a vertebra adjacent the intervertebral disc space.

9. The method of claim 1 further comprising anchoring the second half of the articulating intervertebral disc prosthesis to bone or annulus tissue.

10. The method of claim 1 further comprising limiting expulsion of the second half of the articulating intervertebral disc prosthesis by cutting a stepped cavity adjacent to the opening.

11. The method of claim 1 further comprising connecting the first half to the second half with a tethering device.

12. The method of claim 1 wherein the first half is kidney shaped.

13. The method of claim 1 wherein the first half is oval shaped.

14. The method of claim 1 wherein the first and second halves each comprise an upper shell component, a lower shell component, and a central articulating body, wherein the central articulating bodies are curved to permit a single arc of motion between the central articulating bodies and the respective upper shell components and a single arc of motion between the central articulating bodies and the respective lower shell components.

15. The method of claim 1 wherein the first and second halves each comprise three distinct components.

16. The method of claim 1 wherein the first and second halves each comprise an upper shell component, a lower shell component and a central body.

17. The method of claim 16 wherein each central body articulates between each upper shell component and a lower shell component, respectively.

18. A method for implanting an articulating intervertebral disc prosthesis into an intervertebral disc space, wherein the intervertebral disc space is composed of a first lateral side and a second lateral side, the method comprising:

surgically accessing the intervertebral disc space;

inserting a first half of the articulating intervertebral disc prosthesis into the intervertebral disc space;

inserting a second half of the articulating intervertebral disc prosthesis into the intervertebral disc space, wherein the first half of the intervertebral disc prosthesis is separate from and not connected to the second half of the intervertebral disc prosthesis, and wherein the first and second halves each comprise three distinct components;

positioning the first half of the articulating intervertebral disc prosthesis on the second lateral side of the intervertebral disc space such that the entirety of the first half of the articulating disc prosthesis is situated on the second lateral side of the intervertebral disc space;

and positioning the second half of the articulating intervertebral disc prosthesis on the first lateral side of the intervertebral disc space such that the entirety of the second half of the articulating disc prosthesis is situated on the first lateral side of the intervertebral disc space;

the step of surgically accessing the intervertebral disc space is done through a single opening on a posterior side of the intervertebrat disc space and on the first lateral side of the intervertebral disc space; and wherein the first half takes an arcuate path from the first lateral side to the second lateral side.

19. The method of claim 18 wherein at least a portion of the arcuate path is milled into an endplate of a vertebra adjacent the intervertebral disc space.

20. A method for implanting an articulating intervertebral disc prosthesis into an intervertebral disc space, wherein the intervertebral disc space is composed of a first lateral side and a second lateral side, the method comprising:

surgically accessing the intervertebral disc space;

inserting a first half of the articulating intervertebral disc prosthesis into the intervertebral disc space;

inserting a second half of the articulating intervertebral disc prosthesis into the intervertebral disc space, wherein the first half of the intervertebral disc prosthesis is separate from and not connected to the second half of the intervertebral disc prosthesis, and wherein the first and second halves each comprise three distinct components;

positioning the first half of the articulating intervertebral disc prosthesis on the second lateral side of the intervertebral disc space such that the entirety of the first half of the articulating disc prosthesis is situated on the second lateral side of the intervertebral disc space; and positioning the second half of the articulating intervertebral disc prosthesis on the first lateral side of the intervertebral disc space such that the entirety of the second half of the articulating disc prosthesis is situated on the first lateral side of the intervertebral disc space;

the step of surgically accessing the intervertebral disc space is done through a single opening on a posterior side of the intervertebrat disc space and on the first lateral side of the intervertebral disc space; and wherein the first half takes a generally linear path from the first lateral side to the second lateral side.

21. A method for implanting an articulating intervertebral disc prosthesis into an intervertebral disc space, wherein the intervertebral disc space is composed of a first lateral side and a second lateral side, the method comprising:

surgically accessing the intervertebral disc space;

inserting a first half of the articulating intervertebral disc prosthesis into the intervertebral disc space;

inserting a second half of the articulating intervertebral disc prosthesis into the intervertebral disc space, wherein the first half of the intervertebral disc prosthesis is separate from and not connected to the second half of the intervertebral disc prosthesis, and wherein the first and second halves each comprise three distinct components;

positioning the first half of the articulating intervertebral disc prosthesis on the second lateral side of the intervertebral disc space such that the entirety of the first half of the articulating disc prosthesis is situated on the second lateral side of the intervertebral disc space; and positioning the second half of the articulating intervertebral disc prosthesis on the first lateral side of the intervertebral disc space such that the entirety of the second half of the articulating disc prosthesis is situated on the first lateral side of the intervertebral disc space;

the step of surgically accessing the intervertebral disc space is done through a single opening on a posterior side of the intervertebrat disc space and on the first lateral side of the intervertebral disc space; wherein the intervertebral disc space is defined by two adjacent vertebral bodies, at least one of which having an anterior side that is arcuate in shape, and wherein the first half takes an arcuate path from the first lateral side to the second lateral side, wherein the arcuate path is defined by the arcuate shape of the anterior side of the at least one vertebral body.

* * * * *